US010869631B2

(12) United States Patent
Potes et al.

(10) Patent No.: US 10,869,631 B2
(45) Date of Patent: Dec. 22, 2020

(54) METHOD AND SYSTEM FOR ASSESSING FLUID RESPONSIVENESS USING MULTIMODAL DATA

(71) Applicant: KONINKLIJKE PHILIPS N.V., Eindhoven (NL)

(72) Inventors: Cristhian Potes, Salem, NH (US); Bryan Conroy, Garden City South, NY (US); Adam Jacob Seiver, Los Altos Hills, CA (US); Minnan Xu, Cambridge, MA (US); Larry James Eshelman, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 570 days.

(21) Appl. No.: 15/536,163

(22) PCT Filed: Dec. 9, 2015

(86) PCT No.: PCT/IB2015/059456
§ 371 (c)(1),
(2) Date: Jun. 15, 2017

(87) PCT Pub. No.: WO2016/097935
PCT Pub. Date: Jun. 23, 2016

(65) Prior Publication Data
US 2017/0360366 A1    Dec. 21, 2017

Related U.S. Application Data

(60) Provisional application No. 62/092,858, filed on Dec. 17, 2014.

(51) Int. Cl.
*A61B 5/00*    (2006.01)
*A61M 5/172*    (2006.01)
(Continued)

(52) U.S. Cl.
CPC .......... *A61B 5/4848* (2013.01); *A61B 5/0205* (2013.01); *A61B 5/0245* (2013.01);
(Continued)

(58) Field of Classification Search
CPC .......... A61M 2005/14208; A61M 2005/1723; A61M 2205/52; A61M 2205/50;
(Continued)

(56) References Cited

U.S. PATENT DOCUMENTS 5,860,917 A    1/1999    Comanor et al.
8,298,151 B2   10/2012   Riobo Aboy et al.
(Continued)

FOREIGN PATENT DOCUMENTS

RU    110950 U1    12/2011
WO   2014152260 A1   9/2014

*Primary Examiner* — Jenna Zhang

(57) ABSTRACT

A system (100) for assessing fluid responsiveness includes an infusion pump (24) in communication with at least one processor (32), and a plurality of physiological monitors (40,42,44,46) operable to receive physiological signals from an associated patient. Physiological signals (48,50) acquired from the associated patient (10) during a fluid challenge are synchronized with a timing signal (54) of the infusion pump (24) administering the fluid challenge. One or more dynamic indices and/or features (58) is calculated from the synchronized physiological signals (50), and one or more dynamic indices and/or features (50) is calculated from baseline physiological signals (48) acquired from the associated patient (10) prior to the fluid challenge. A fluid responsiveness probability value (64) of the patient (10) is determined based on dynamic indices and/or features (58) from the synchronized physiological signals (50) and dynamic indices and/or features (50) from the baseline physiological signals (48).

20 Claims, 4 Drawing Sheets

(51) Int. Cl.
| | |
|---|---|
| *A61B 5/0205* | (2006.01) |
| *A61B 5/0245* | (2006.01) |
| *A61B 5/083* | (2006.01) |
| *A61B 5/0456* | (2006.01) |
| *A61B 5/0432* | (2006.01) |
| *A61B 5/024* | (2006.01) |
| *G06F 19/00* | (2018.01) |
| *G16H 20/10* | (2018.01) |
| *G16H 20/17* | (2018.01) |
| *A61B 5/021* | (2006.01) |
| *A61M 5/142* | (2006.01) |
| *A61B 5/02* | (2006.01) |
| *A61B 5/08* | (2006.01) |
| *A61B 5/087* | (2006.01) |
| *A61B 5/091* | (2006.01) |

(52) U.S. Cl.
CPC ...... *A61B 5/02405* (2013.01); *A61B 5/02416* (2013.01); *A61B 5/0456* (2013.01); *A61B 5/04325* (2013.01); *A61B 5/0836* (2013.01); *A61B 5/4833* (2013.01); *A61B 5/4839* (2013.01); *A61B 5/7267* (2013.01); *A61B 5/7289* (2013.01); *A61M 5/1723* (2013.01); *G06F 19/3456* (2013.01); *G16H 20/10* (2018.01); *G16H 20/17* (2018.01); *A61B 5/021* (2013.01); *A61B 5/02028* (2013.01); *A61B 5/02055* (2013.01); *A61B 5/082* (2013.01); *A61B 5/087* (2013.01); *A61B 5/091* (2013.01); *A61B 5/742* (2013.01); *A61B 5/746* (2013.01); *A61M 2005/14208* (2013.01); *A61M 2205/50* (2013.01); *A61M 2205/52* (2013.01); *G06F 19/3468* (2013.01)

(58) Field of Classification Search
CPC ... A61B 5/7289; A61B 5/4839; A61B 5/4848; A61B 5/4833; A61B 5/746; A61B 5/742; A61B 5/04325; A61B 5/02416; A61B 5/02405; A61B 5/0456; A61B 5/0836; A61B 5/0245; A61B 5/0205; A61B 5/02055; A61B 5/091; A61B 5/087; A61B 5/082; A61B 5/0228; A61B 5/021; G16H 20/10; G16H 20/17; G16H 20/60; G16H 20/70; G16H 20/90; G06F 19/3456; G06F 19/3468

See application file for complete search history.

(56) References Cited

U.S. PATENT DOCUMENTS

| | | | |
|---|---|---|---|
| 8,532,754 | B2 | 9/2013 | Cannesson |
| 8,617,135 | B2 | 12/2013 | Rinehart et al. |
| 8,880,155 | B2 | 11/2014 | Mestek et al. |
| 2004/0254525 | A1 | 12/2004 | Uber, III et al. |
| 2005/0177096 | A1 | 8/2005 | Bollish et al. |
| 2006/0289020 | A1 | 12/2006 | Tabak et al. |
| 2009/0124867 | A1* | 5/2009 | Hirsh ................ A61M 16/0051 600/301 |
| 2010/0081942 | A1* | 4/2010 | Huiku ................ A61B 5/02028 600/483 |
| 2011/0077474 | A1 | 3/2011 | Huiku |
| 2014/0073889 | A1* | 3/2014 | Su ..................... A61M 16/0051 600/324 |
| 2014/0073890 | A1* | 3/2014 | Su ....................... A61B 5/1455 600/324 |
| 2014/0323876 | A1 | 10/2014 | McGonigle et al. |
| 2015/0080669 | A1 | 3/2015 | Settels et al. |
| 2015/0231363 | A1 | 8/2015 | Uber, III et al. |

* cited by examiner

METHOD AND SYSTEM FOR ASSESSING FLUID RESPONSIVENESS USING MULTIMODAL DATA

CROSS-REFERENCE TO PRIOR APPLICATIONS

This application is the U.S. National Phase application under 35 U.S.C. § 371 of International Application No. PCT/IB2015/059456, filed on Dec. 9, 2015, which claims the benefit of U.S. Provisional Application Serial No. 62/092,858, filed Dec. 17, 2014. These applications are hereby incorporated by reference herein, for all purposes.

The present application relates generally to the medical arts. It finds a particular application in conjunction with medical monitoring, patient treatment, and the like, for use in hospitals, urgent care centers, emergency and/or trauma treatment, fluid resuscitation, and the like. However, it is to be understood that it also finds application in other usage scenarios and is not necessarily limited to the aforementioned applications.

Fluid resuscitation is the first step in treating critically-ill patients who have been recognized as hemodynamically unstable. Unfortunately, only 50% of critically-ill patients in the operating room (OR), intensive care unit (ICU), or emergency department (ED) respond favorably to fluid resuscitation. Furthermore, those patients who do not respond favorably may be harmed by the treatment itself and consequently develop other clinical problems such as pulmonary or tissue edema. A predictive procedure for ascertaining whether a patient will be responsive to fluid resuscitation is by measuring changes in cardiac output before and after a fluid or mini-fluid challenge. Such a fluid challenge is a technique that consists of giving a small amount of intravenous fluids in a short period of time (also known as fluid bolus). By doing so, the clinician can assess whether the patient has a preload reserve that can be used to increase the stroke volume with further fluids.

In normal individuals who are spontaneously breathing, the arterial blood pressure (ABP), R peak of electrocardiography (ECG), or amplitude in plethysmography (PPG) decreases during inspiration and increases during expiration. The normal fall in systolic blood pressure is less than 10 mmHg. When the fall in pressure during inspiration is more than 10 mmHg, this phenomenon is called pulsus paradoxus. A reverse of this phenomenon, i.e., systolic blood pressure, R peak, or PPG amplitude increases during inspiration and decreases during expiration, has been reported during positive pressure breathing (e.g., in patients who are mechanically ventilated).

Dynamic indices derived from variations in ABP, ECG, or PPG with the respiratory cycle, i.e., pulse pressure variability (PPV), stroke volume variability (SVV), systolic pressure variability (SPV), RR variability (RRV), and pleth variability (PVI) (http://www.masimo.com/pvi/), have been shown to be very good predictors of fluid responsiveness (i.e., predicting an increased in stroke volume by 10-15% after fluid administration) in mechanically ventilated patients. Unfortunately, these dynamic indices are not accurate in predicting fluid responsiveness in spontaneously breathing patients, mainly because the variations of ABP, ECG, or PPG with the respiratory cycles are not very prominent (i.e., very low signal to noise ratio). It is worthy to mention that to assess fluid responsiveness in mechanically ventilated patients using these dynamic indices, patients do not need to undergo a fluid challenge.

The present application provides new and improved methods and systems which overcome the above-referenced challenges.

In accordance with one aspect, a system for assessing fluid responsiveness is disclosed, comprising: at least one processor and an infusion pump in communication with the at least one processor, and a plurality of physiological monitors operable to receive physiological signals from an associated patient. The at least one processor is programmed to synchronize physiological signals acquired from the associated patient during a fluid challenge with a timing signal of the infusion pump administering the fluid challenge; calculate one or more dynamic indices and/or features from the synchronized physiological signals; and determining a fluid responsiveness probability value of the patient using the one or more dynamic indices and/or features from the synchronized physiological signals.

In accordance with another aspect, a fluid responsiveness assessing method is disclosed, comprising: receiving a plurality of physiological signals from a plurality of physiological monitors of an associated patient; receiving an infusion pump timing signal corresponding to an infusion of fluids by an associated infusion pump in association with a fluid-challenge administered to the associated patient; synchronizing the timing signal with the received physiological signals so as to generate a synched physiological signal; calculating at least one of a plurality of dynamic indices and/or features from synched fluid-challenge physiological signals; and calculating a fluid responsiveness probability value indicative of a responsiveness of the associated patient to fluid resuscitation.

In accordance with certain other disclosed aspects, a computer medium is disclosed storing instructions executable to control a computer and display to perform the method of the immediately preceding paragraph, and a system for assessing responsiveness of an associated patient to fluid resuscitation including a processor programmed to perform the method of the immediately preceding paragraph.

One advantage resides in providing a systematic procedure to track stroke volume variations as a function of volume and rate of fluids administered to the patient.

Another advantage resides in assessing fluid responsiveness in non-mechanically ventilated patients.

Another advantage resides in minimizing fluid input for non-responsive patients.

Still further advantages of the presently disclosed embodiments will be appreciated by those of ordinary skill in the art upon reading and understanding the following detailed description.

The presently disclosed embodiments may take form in various components and arrangements of components, and in various steps and arrangements of steps. The drawings are only for purposes of illustrating the preferred embodiments and are not to be construed as limiting the presently disclosed embodiments.

FIG. 1 diagrammatically illustrates a medical environment including a patient monitor including monitoring instruments configured to assess patient response to fluid resuscitation.

Figure 1:
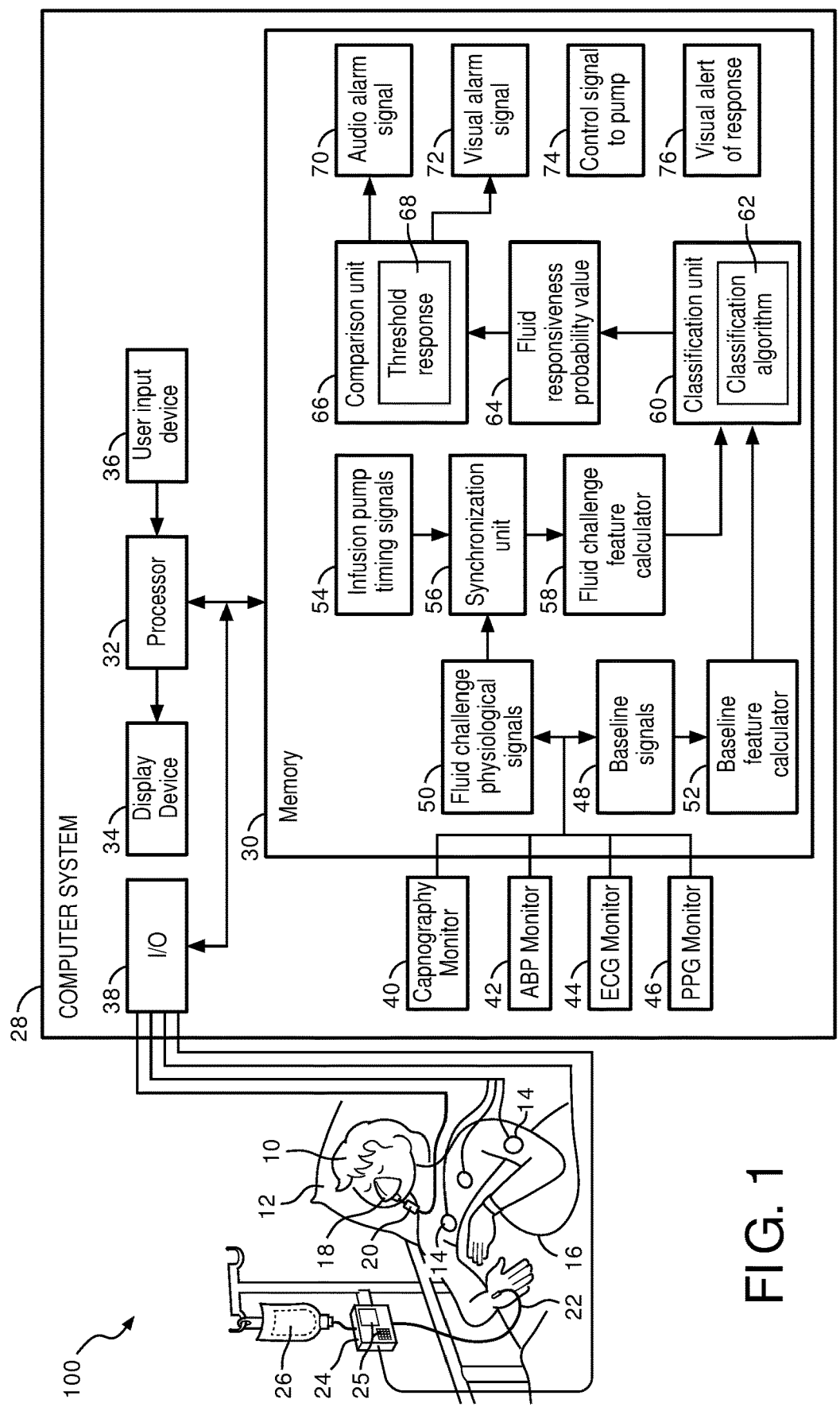

With reference to FIG. 1, a fluid response assessment system 100 is depicted illustrating a patient 10 shown lying in a bed 12 such as is a typical situation in a hospital, emergency room, intensive care unit (ICU), cardiac care unit (CCU), or so forth. Depending upon the patient's condition, it is also contemplated that the patient 10 may be ambulatory, residing in a wheel chair, seated in a chair, or so forth. The patient is monitored by various medical monitoring devices, including in the illustrated embodiment an electrocardiographic (ECG) instrument with ECG electrodes 14, a blood pressure monitor 16, which may for example be a wholly non-invasive sphygmometer or a minimally invasive arterial line, a plethysmograph (PPG) 18, and a capnograph 20.

The illustrated blood pressure monitor 16 is wrist-based; however, a blood pressure monitor located on the upper arm or elsewhere on the patient 10 is also contemplated. If an arterial line is used to measure blood pressure, it may optionally be incorporated into an intravenous fluid delivery line or the like. The ECG 14, arterial blood pressure (ABP) monitor 16, PPG 18, and capnograph 20 further include associated electronics for generating and optionally performing signal processing on ECG, blood pressure signals, changes in volume within an organ or body (blood or air), and $CO_2$ pressure in respiratory gases.

The fluid response assessment system 100, as depicted in FIG. 1, includes an intravenous (IV) component comprising a fluid 26, infusion pump 24, and line 22 for transferring the fluid 26 into the patient 10. The infusion pump 24 may be implemented as a rapid infusion pump that is programmable via the computer system 28, remotely programmable, programmable via a user input component 25 (touch screen/keypad/touchpad, etc.), or the like. In some embodiments, the infusion pump 24 is programmed to administer a selected quantity of fluid 26 to the patient 10 during a predetermined time interval, e.g., a fluid challenge, also referenced as a mini-fluid challenge. The fluid challenge, as used in such settings, allows for an assessment of whether or not a patient 10 will respond to fluid resuscitation. The fluid challenge referenced herein corresponds to a limited amount of fluid 26 infused into the patient 10 during a discrete time interval, as opposed to the general provisioning of fluids. The system 100 further includes a computer system 28 in communication with the infusion pump 24, the various electrodes 14, monitor 16, plethysmograph 18, and capnograph 20 via an I/O interface 38. According to one embodiment, the I/O interface 38 may communicate, via suitable communications links, with one or more of the various patient monitoring components 14, 16, 18, 20, a computer network (not shown), external display device (not shown), or other suitable input or output electronic device. The system 100 may further include additional physiological monitoring devices, e.g., pulse oximeter, thermometer, glucose monitor, and the like.

The computer system 28 coordinates the operations of the system 100, and may be remotely positioned therefrom. The computer system 28 includes at least one processor 32 and at least one program memory 30. The program memory 30 includes processor executable instructions that, when executed by the processor 32, coordinate the operation of the computer system 28, including physiological signal analysis and processing, classification of fluid response, alarm generation, and the like. The processor 32 executes the processor executable instructions stored in the program memory 30.

The computer system 28 further comprises electronics providing for capnography monitoring 40, ABP monitoring 42, ECG monitoring 44, and PPG monitoring 46. Although not depicted in FIG. 1, the computer system 28 may optionally provide electronics for monitoring selected other physiological parameters such as respiration rate based on suitable physiological input signals. The computer system 28 includes a processor 32 operable to control operations of the computer system 28, facilitate processing of physiological signals, execute instructions, perform calculations, facilitate comparisons and storage of various inputs and the like.

The computer system 28 further includes a display device 34 in communication with the processor 32 and configured to display one or more displaying information such as physiological signals, test results, patient information, vitals, graphical user interface, alerts, and the like, and a user input device 36, such as a keyboard or touch or writable screen, for inputting text, and/or a cursor control device, such as a mouse, trackball, or the like, for communicating user input information and command selections to the processor 32. In one embodiment, the display device 34 may be implemented as an integrated multi-functional patient monitor these electronics may be embodied within a unitary multi-functional patient monitor (not shown) that an integrated display of the resulting processed ECG, ABP, PPG, and/or capnography signals. The display device 34 may display measured physiological parameters such as the ECG trace, blood pressure (BP) data, respiratory data, or so forth. The display can display these parameters in various ways, such as by current numerical value, by a trace showing parameter value as a function of time, or so forth.

Figure 2:
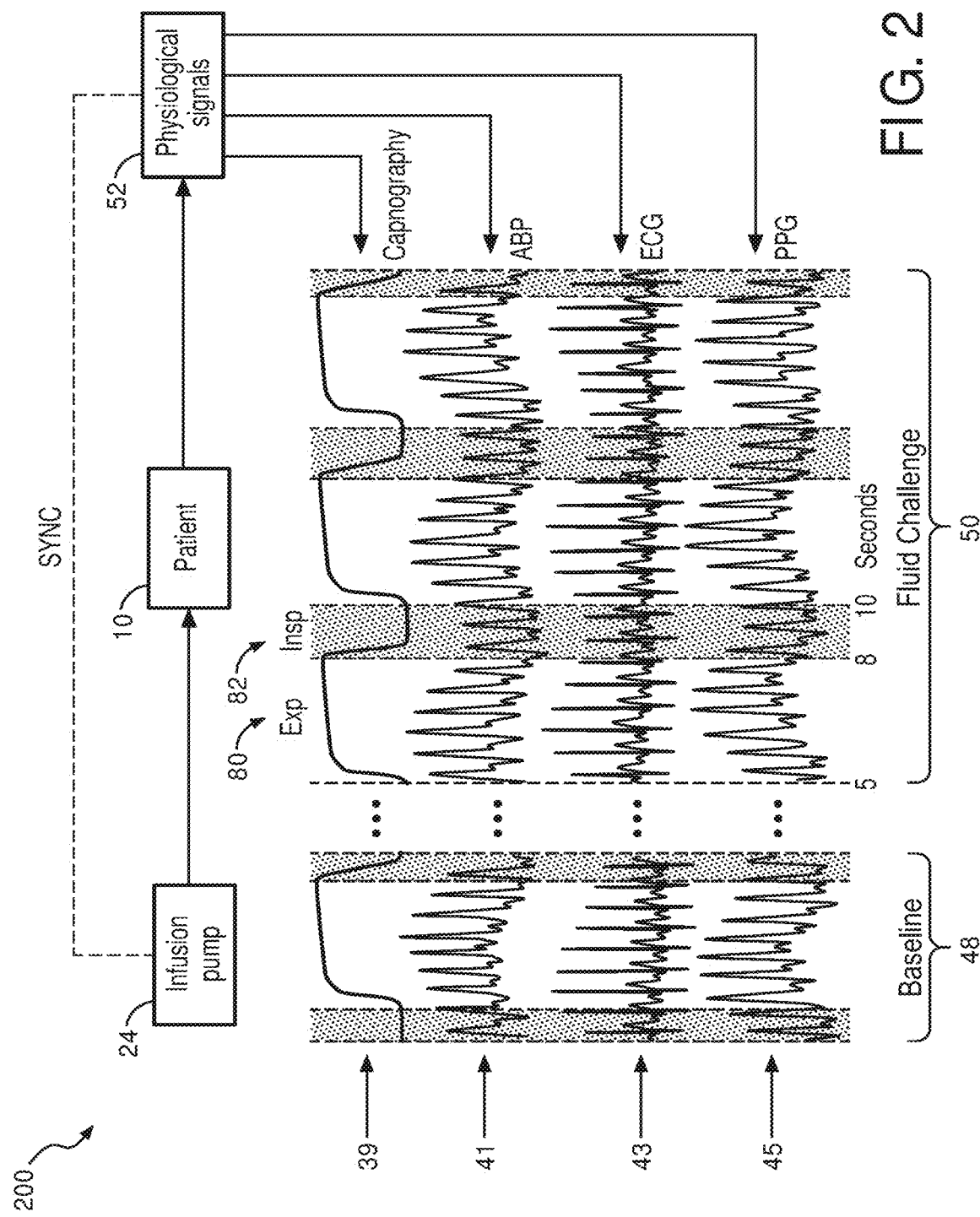
FIG. 2 illustrates baseline and fluid challenge physiological signals acquired from a patient for use in assessing fluid responsiveness.

A baseline signal module 48 of the processor executable instructions stored in memory 30 controls receipt of physiological signals from the monitors 40, 42, 44, and 46 of the patient 10 prior to administration of the fluid 26 during a fluid challenge. As discussed in greater detail below, FIG. 2 provides an illustration of baseline physiological signals 39, 41, 43, 45 received via monitors 40, 42, 44, 46. A baseline feature calculator 52 of the processor executable instructions facilitates the derivation from the baseline physiological signals 48, i.e., calculation, of dynamic indices and/or features from variations in ABP, ECG, or PPG with the respiratory cycle, i.e., pulse pressure variability (PPV), stroke volume variability (SVV), and systolic pressure variability (SPV). According to one embodiment, the dynamic indices may be calculated as follows:

$$SVV = \frac{SV_{max}(\exp) - SV_{min}(insp)}{(SV_{max}(\exp) + SV_{min}(insp))/2}; \quad (1)$$

$$SPV = \frac{SP_{max}(\exp) - SP_{min}(insp)}{(SP_{max}(\exp) + SP_{min}(insp))/2}; \text{ and} \quad (2)$$

$$PPV = \frac{PP_{max}(\exp) - PP_{min}(insp)}{(PP_{max}(\exp) + PP_{min}(insp))/2}. \quad (3)$$

Additional dynamic indices and/or features may include RR variability (RRV), and pleth variability index (PVI). RRV may correspond to the variation in the time interval between heartbeats, i.e., measured by the variation in the beat-to-beat interval. The R-R variability (RRV) utilizes the interval between successive R's, where R is a peak of a QRS complex and RRV corresponds to the peak to peak of successive QRS complexes of the ECG wave. The pleth variability index (PVI) is a measurement associated with respiratory variations in pulse oximetry plethysmographic waveform amplitude for prediction of fluid responsiveness.

The baseline feature calculator 52 may further calculate various features, e.g., volumetric capnography, end-tidal $CO_2$ derived from capnography, cardiac output derived from ABP, or the like, from the baseline physiological signals 48. Physiological signals vary during the respiratory cycle, inhalation (inspiration) 82 and exhalation (expiration) 80. For example, in spontaneously breathing patients, during exhalation (expiration) 80 of the respiratory cycle, blood pressure increases while during the inhalation (inspiration) 82 of the respiratory cycle, blood pressure decreases.

Accordingly, the baseline feature calculator 52 is suitably configured to calculate the dynamic indices and/or features during the inspiration portion 82 of the respiratory cycle and during the expiration portion 80 of the respiratory cycle. In one embodiment, the dynamic indices and/or features utilized pertain to only the inspiration portion 82 of the cycle or the expiration portion 80 of the respiratory cycle.

A fluid challenge physiological signal module 50 of the processor executable instructions stored in memory 30 controls receipt of physiological signals from monitors 40, 42, 44, 46 taken after beginning the administration of the fluid 26 from the IV component during a fluid challenge for ascertaining whether the patient 10 is responsive to fluid resuscitation. An infusion pump timing signal module 54 of the processor executable instructions receives an output from the infusion pump 24 during the fluid challenge corresponding to the automated fluid administration to the patient 10 by the pump 24. A synchronization unit 56 of the processor executable instructions synchronizes the timing signal 54 of the infusion pump 24 with the fluid challenge physiological signals 50 so as to indicate the amount of fluid 26 provided to the patient 10 in correlation with the corresponding physiological signal at a given time.

A fluid challenge feature calculator 58 of the processor executable instructions facilitates the derivation from the synchronized fluid challenge physiological signals 50, i.e., calculation, of dynamic indices and/or features from variations in ABP, ECG, or PPG with the respiratory cycle, e.g., PPV, SVV, SPV, RRV, and PVI. The fluid challenge feature calculator 58 may further calculate various features, e.g., volumetric capnography, end-tidal $CO_2$ derived from capnography, cardiac output derived from ABP, or the like, from the synchronized physiological signals 50 output via the synchronization unit 56. The fluid challenge feature calculator 58 is suitably configured to calculate the dynamic indices and/or features during the inspiration portion 82 of the respiratory cycle and during the expiration portion 80 of the respiratory cycle occurring during administration of the fluid challenge. In one embodiment, the dynamic indices and/or features utilized pertain to only the inspiration portion 82 of the cycle or the expiration portion 80 of the respiratory cycle during the administration of the fluid challenge. That is, the dynamic indices and/or features 52 and 58 are calculated using respective physiological signals 48 and 50 reflecting the inspiration portion 82 of the respiratory cycle of the associated patient 10. The respiratory cycle of the patient 10 may be determined in accordance with the operations of the capnography monitor 40.

A classification unit 60 of the processor executable instructions employs a classification algorithm 64 e.g., a probabilistic classification model, to which the fluid challenge features and/or indices 58 and baseline features and/or indices 52 are input to generate a fluid responsiveness probability value 66. In accordance with one embodiment, the application of the classification algorithm 64 corresponds to the use of the features and/or indices from the baseline 52 and the fluid challenge 58 as inputs to a logistic regression algorithm. The classification algorithm 64 may be developed or trained during previous fluid challenges or preselected medical inputs based upon the age, weight, height, gender, race, or other medically relevant data. As discussed above, the features may include dynamic indices (SVV, SPV, PPV, RRV, PVI), volumetric capnography, end-tidal $CO_2$, cardiac output, or the like. As previously addressed, the dynamic indices and/or other features may correspond to physiological signals collected during only the inspiration or expiration portion of the respiratory cycle of the patient 10 to whom the fluid challenge is being administered. The fluid responsiveness probability value 64 represents a score indicating the likelihood of the patient 10 responding favorably to fluid resuscitation. In accordance with one embodiment, the probability value 64 varies from 0 (i.e., the patient 10 is not responsive) to 1 (i.e., the patient 10 is responsive to fluids).

A comparison unit 66 of the processor executable instructions facilitates comparison of the fluid responsiveness probability value 64 to a threshold response value 68. The threshold response value 68 corresponds to a threshold at or above which the patient 10 is responsive to fluid resuscitation and below which the patient 10 is not responsive to fluid resuscitation. The fluid resuscitation assessment system 100 of FIG. 1 provides several exemplary outputs with respect to the result of the comparison unit 66. As depicted therein, upon a determination that the fluid responsiveness probability value 64 falls below the predetermined threshold 68, the processor executable instructions include an audio alarm signal 70, a visual alarm signal 72, a control signal 74 to the infusion pump 24 (stop fluid challenge), and the like. The alarm signals 70 may utilize suitable auditory devices, e.g., speaker 78, whereas the alarm signal 72 may utilize the display device 34 to provide a visual depiction of the ineffectiveness or non-responsiveness of the patient 10 to fluid resuscitation, e.g., flashing graphic, blinking light, or myriad other suitable visually descriptive devices or indicia. The control signal 74 output to the infusion pump 24 may indicate to the pump 24 to immediately cease infusion of fluid 26 to the patient 10, as discussed above, such fluid infusion may be harmful to a non-responding patient 10. Alternatively, such signal 74 may be interpreted by the pump 24 to begin emitting suitable auditory and/or visual queues to physicians, nurses, or the like, of the non-responsiveness of the patient 10. When the fluid responsiveness probability value 64 of the patient 10 meets or exceeds the threshold 66, the processor executable instructions of the system 100 include a visual alert 76 of the responsiveness of the patient 10 to fluid resuscitation. As a non-limiting example, the display device 34 may produce a graphic, or other indicia reflecting the patient's positive response to fluid resuscitation.

The computer system 28 may include a computer server, workstation, personal computer, cellular telephone, tablet computer, pager, combination thereof, or other computing device capable of executing instructions for performing the exemplary method.

According to one example embodiment, the computer system 28 includes hardware, software, and/or any suitable combination thereof, configured to interact with an associated user, a networked device, networked storage, remote devices, or the like.

The memory 30 may represent any type of non-transitory computer readable medium such as random access memory (RAM), read only memory (ROM), magnetic disk or tape, optical disk, flash memory, or holographic memory. In one embodiment, the memory 30 comprises a combination of random access memory and read only memory. In some embodiments, the processor 32 and the memory 30 may be combined in a single chip. The I/O interface 38 may allow the computer system 28 to communicate with other devices via a computer network, and may comprise a modulator/demodulator (MODEM). Memory 30 may store data processed in the method as well as the instructions for performing the exemplary method.

The processor 32 can be variously embodied, such as by a single core processor, a dual core processor (or more generally by a multiple core processor), a digital processor and cooperating math and/or graphics coprocessor, a digital controller, or the like. The processor 32 in addition to controlling the operation of the computer system 28, executes instructions and units stored in the memory 30 for performing the method outlined in FIG. 4.

The term "software," as used herein, is intended to encompass any collection or set of instructions executable by a computer or other digital system so as to configure the computer or other digital system to perform the task that is the intent of the software. The term "software," as further used herein, is intended to also encompass such instructions stored in storage mediums, such as RAM, a hard disk, optical disk, or so forth, and is intended to encompass so-called "firmware" that is software stored on a ROM or so forth. Such software may be organized in various ways, and may include software components organized as libraries, Internet-based programs stored on a remote server or so forth, source code, interpretive code, object code, directly executable code, and so forth. It is contemplated that the software may invoke system-level code or calls to other software residing on a server or other location to perform certain functions.

Turning now to FIG. 2, there is shown an illustrative example 200 of the functioning of the system 100 in accordance with one example embodiment. As shown in FIG. 2, baseline physiological signals 48 are depicted to the left prior to commencement of a fluid challenge to the patient 10. The baseline physiological signals 48 used in the illustrative example 200 include a capnography signal 39 (via capnography monitor 40), an ABP signal 41 (via ABP monitor 42), an ECG signal 43 (via ECG monitor 44), and a PPG signal 45 (via PPG monitor 46). These signals 48 are stored in memory 30 and used for generation of dynamic indices and/or features 52 as discussed above. After the infusion pump 24 begins the systematic administration of fluids, i.e., the fluid challenge, physiological signals 50 are collected for the patient 10 and time synchronized with the operation of the pump 24. As shown, the expiration phase 80 and the inspiration phase 82 (as shaded) are distinguishable from each other and impact the signals 48, 50 collected from the patient. Expiration 80 and inspiration 82 phases of the respiratory cycle may be identified from the capnography signal 39, or be estimated from the ABP signal 41, the ECG signal 43, or the PPG signal 45.

Figure 3:
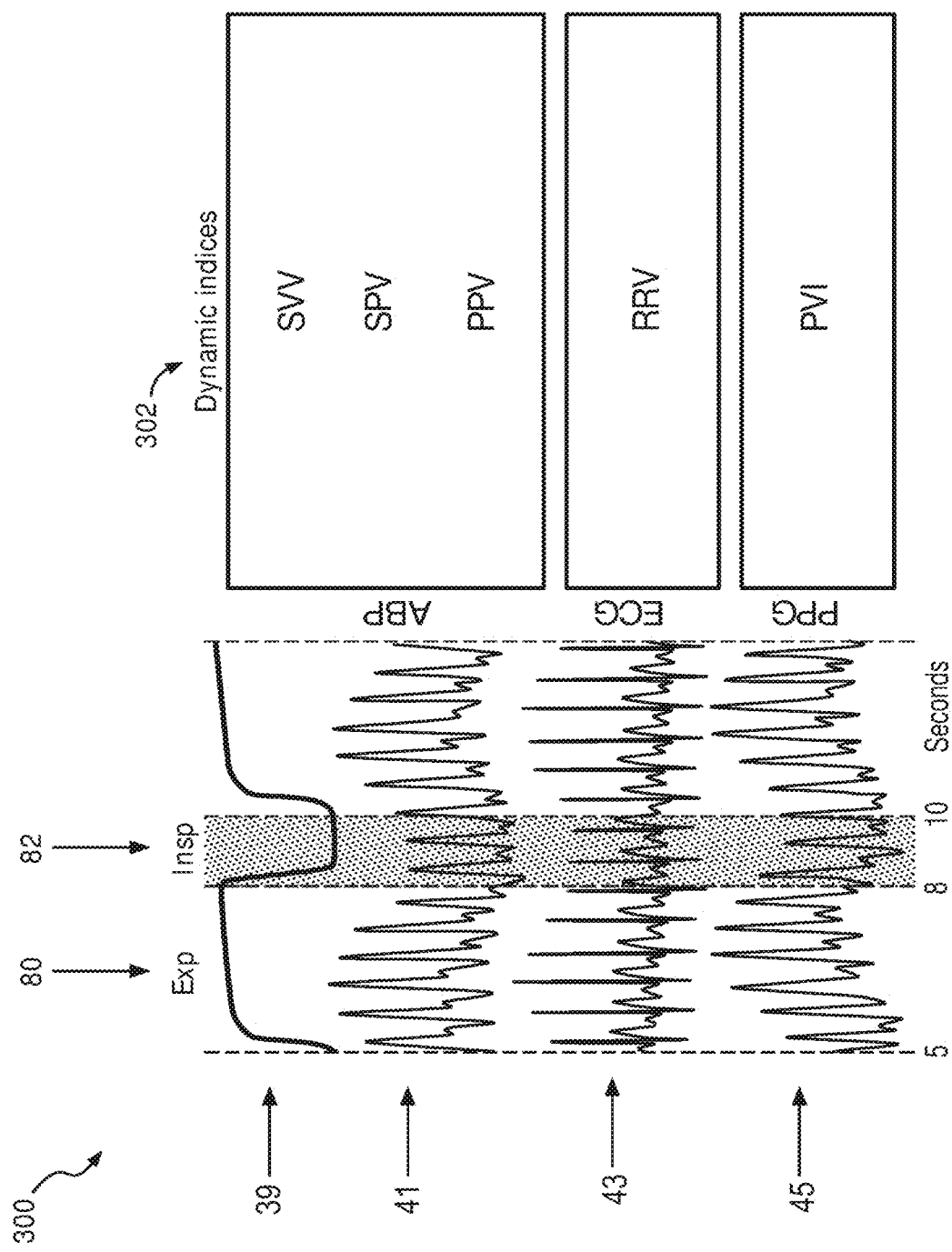
FIG. 3 illustrates dynamic indices and/or features of fluid challenge physiological signals acquired from a patient for use in assessing fluid responsiveness.

FIG. 3 illustrates the collected physiological signals (48, 50) and the corresponding dynamic indices 302 derived therefrom. As shown, SVV, SPV, and PPV are derived from the ABP signal 41. RRV is derived from the received ECG signal 43 as discussed above. PVI is derived from the PPG signal 45 as discussed above. The dynamic indices 302 take advantage of the respiratory variations in the ABP signal 41, the ECG signal 43, or the PPG signal 45 to assess fluid responsiveness. These dynamic indices 302, in addition to the features 52, 58, are utilized via the classification unit 60 to calculate a fluid responsiveness probability value 64.

Figure 4:
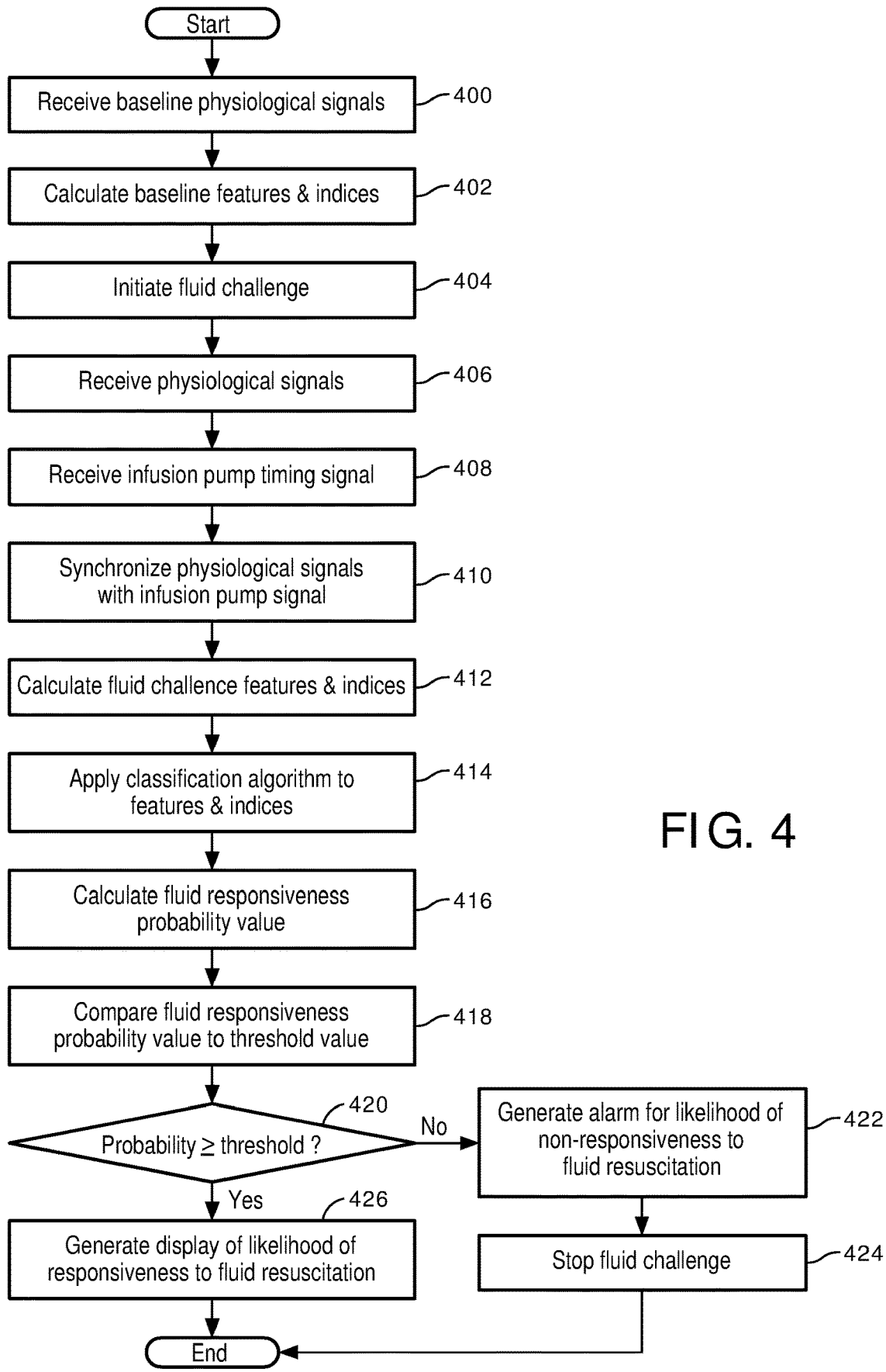
FIG. 4 illustrates a method for assessing fluid responsiveness.

Turning now to FIG. 4, there is shown a flowchart describing one example implementation of a method for assessing fluid responsiveness in accordance with one embodiment. The methodology begins at 400, whereupon baseline physiological signals 48 are received from the various electrodes 14, monitor 16, plethysmograph 18, and capnograph 20 by the capnography monitor 40, ABP monitor 42, ECG monitor 44, and PPG monitor 46 via an I/O interface 38. Baseline features and indices 52, e.g., SVV, SPV, PPV, RRV, PVI, volumetric capnography, end-tidal $CO_2$ derived from capnography, cardiac output derived from ABP, are then calculated at 402 via the processor 32 or other suitable component associated with the computer system 28.

At 404, a fluid challenge is initiated on the patient 10 via the infusion of fluid 26 by the infusion pump 24 in accordance with a preset amount, speed, and duration of administration of the fluid 26. In accordance with one embodiment, an example fluid challenge is a "mini-fluid challenge" corresponding to an infusion of 100 ml of colloid over 1 min. Other mini-challenges or fluid challenges may be utilized in accordance with the systems and methods set forth herein depending upon the type of fluid being used, the apparent condition of the patient 10, the experience of the doctor, or other factors. An example of a regular fluid challenge may administer 500 mL of a fluid over 10-30 minutes.

At 406, physiological signals 50 of the patient 10 during the fluid challenge are received from the above-noted input devices 14, 16, 18, 20 by the monitors 40, 42, 44, and 46. A timing signal 54 is received from the infusion pump 24 during the fluid challenge at 408. At 410, the fluid challenge physiological signals 50 are synchronized with the infusion pump timing signal 54 via the synchronization unit 56 or other suitable component of the computer system 28. Fluid challenge features and indices 52, e.g., SVV, SPV, PPV, RRV, PVI, volumetric capnography, end-tidal $CO_2$ derived from capnography, cardiac output derived from ABP, are then calculated at 412 via the processor 32 or other suitable component associated with the computer system 28. According to one embodiment, the various dynamic indices and/or features 52 and 58 may be calculated during the expiration phase or portion 80 of the respiratory cycle of the patient. In such an embodiment, the expiration portion 80 of the respiratory cycle provides greater variations for analysis by the ABP monitor 42, ECG monitor 44, PPG monitor 46, as well as the calculations described above, as illustrated in FIGS. 2-3.

The classification algorithm 62 is then utilized by the classification unit 60 or other suitable component associated with the computer system 28 with the baseline features and/or dynamic indices 52 and the fluid challenge features and/or dynamic indices 58 as inputs at 414. As discussed above, the classification algorithm 62 may be a logical regression algorithm that utilizes various features and/or dynamic indices 52, 58 of the patient 10 during the expiration 80 or inspiration 82 portions of the respiratory cycle. A fluid responsiveness probability value 64 is then calculated at 416 representing a probability that the patient 10 is responsive or non-responsive to fluid resuscitation. The fluid responsiveness probability value 64 is representative of a value between 0 and 1, where values closer to 0 indicate that the patient 10 is unlikely to respond or will negatively respond to fluid resuscitation, while values closer to 1 indicate the patient 10 is responding or will respond favorably to fluid resuscitation.

The fluid responsiveness probability value 64 calculated for the patient 10 undergoing the fluid challenge is then compared to a predetermined threshold response value 68 at 418. As discussed above, the threshold response value 68 is selected between 0 and 1, wherein a fluid responsiveness probability value 64 greater than or equal to the threshold value 68 is indicative of a patient 10 that will respond favorably to fluid resuscitation and a probability value 64 less than the threshold value 68 is indicative of a patient 10 that will respond negatively or have no response to fluid resuscitation. The threshold value 68 may be selected in accordance with the fluid 26 being administered, the apparent type of injury or patient condition, the amount of time allotted for the challenge, the discretion of the attending physician, or myriad other medical considerations for IV support of a patient 10.

Accordingly, at 420, a determination is made whether the fluid responsiveness probability value 64 is greater than or less than the preselected threshold value 68. Upon a positive determination at 420, operations proceed to 426, whereupon a visual alert 76 is generated via the display device 34 or other suitable alerting mechanism as to the likelihood of a favorable response to fluid resuscitation by the patient 10. Upon a determination at 420 that the fluid responsiveness probability value 64 is less than the threshold value 68, operations proceed to 422. At 422, an alarm, e.g., audio alarm signal 70, visual alarm signal 72, is generated alerting attending personnel that the patient 10 is likely not responsive to fluid resuscitation or is negatively reacting to the fluid challenge. The fluid challenge, if still being administered, is then terminated at 424 via the control signal 74 communicated to the infusion pump 24. In accordance with one embodiment, the attending physician or other caregiver may adjust the infusion rate of the infusion pump 24 responsive to the alarm 70, 72 as an alternative to terminating the fluid challenge.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system for assessing fluid responsiveness, the system comprising:
   at least one processor;
   an infusion pump, configured to administer a fluid challenge to an associated patient, wherein the infusion pump is in communication with the at least one processor; and,
   a plurality of physiological monitors configured to receive physiological signals from the associated patient, wherein the at least one processor is programmed to:
      receive, from the infusion pump administering the fluid challenge to the associated patient, a timing signal corresponding to an infusion of fluids by the infusion pump during the administration of the fluid challenge to the associated patient;
      synchronize physiological signals acquired from the associated patient during the administration of the fluid challenge with the timing signal of the infusion pump so as to indicate an amount of fluid provided to the associated patient in correlation with the corresponding physiological signals at a given time, wherein each of the physiological signals being synchronized are acquired from a beginning to an end of the fluid challenge;
      calculate one or more dynamic indices and/or features from the synchronized physiological signals; and
      determine a fluid responsiveness probability value of the patient responsive to the one or more dynamic indices and/or features from the synchronized physiological signals.

2. The system according to claim 1, wherein the at least one processor is further programmed to:
   terminate operations of the infusion pump responsive to the fluid responsiveness probability value indicative of the patient being non-responsive to fluid resuscitation.

3. The system according to claim 2, wherein the at least one processor is further programmed to:
   calculate the one or more dynamic indices and/or features from baseline physiological signals acquired from the patient prior to the administration of the fluid challenge, wherein determining the fluid responsiveness probability value of the patient is responsive to the one or more dynamic indices and/or features from the synchronized physiological signals and the one or more dynamic indices and/or features from the baseline physiological signals.

4. The system according to claim 3, wherein determining the fluid responsiveness probability value further comprises:
   inputting the one or more dynamic indices and/or features from the synchronized physiological signals and the one or more dynamic indices and/or features from the baseline physiological signals into a classification algorithm.

5. The system according to claim 4, wherein the fluid responsiveness probability value is between 0 indicating non-responsiveness and 1 indicating responsiveness.

6. The system according to claim 5, wherein the at least one processor is further programmed to:
   compare the determined fluid responsiveness probability value to a preselected threshold value, wherein the associated patient is responsive to fluid resuscitation when the determined fluid responsiveness probability value is greater than or equal to the preselected threshold value.

7. The system according to claim 3, wherein the at least one processor is further programmed to:

calculate the one or more dynamic indices and/or features from the synchronized physiological signals and the one or more dynamic indices and/or features from the baseline physiological signals during an expiration portion of a respiratory cycle of the associated patient.

8. The system according to claim 1, wherein the at least one processor is further programmed to:
generate an alarm in response to the determined fluid responsiveness probability value indicating the associated patient is not responsive to fluid resuscitation.

9. The system according to claim 1, wherein the infusion pump is a rapid infusion pump that is synchronized with the physiological signals and configured to:
infuse a fluid during an expiration portion of a respiratory cycle of the associated patient.

10. The system according to claim 1, wherein the plurality of physiological monitors comprise one or more of a capnography monitor, an arterial blood pressure (ABP) monitor, an electrocardiographic (ECG) monitor, and a plethysmograph (PPG) monitor.

11. The system according to claim 1, wherein the dynamic indices and/or features comprise at least one of pulse pressure variability (PPV), stroke volume variability (SVV), systolic pressure variability (SPV), RR variability (RRV), pleth variability index (PVI), volumetric capnography, end-tidal CO2 derived from capnography, and a cardiac output derived from an arterial blood pressure (ABP).

12. A method for assessing fluid responsiveness, the method comprising:
administering, with an infusion pump, a fluid challenge to an associated patient;
receiving, during the administration of the fluid challenge, a plurality of physiological signals from a plurality of physiological monitors of the associated patient;
receiving an infusion pump timing signal corresponding to the infusion of fluids by the associated infusion pump in association with the administration of the fluid challenge to the associated patient;
synchronizing the timing signal with the received plurality of physiological signals so as to generate synchronized physiological signals to indicate an amount of fluid provided to the associated patient in correlation with the corresponding physiological signals at a given time, wherein each of the plurality of physiological signals being synchronized are acquired from a beginning to an end of the fluid challenge;
calculating at least one of a plurality of dynamic indices and/or features from the synchronized plurality of physiological signals; and
calculating a fluid responsiveness probability value indicative of a responsiveness of the associated patient to fluid resuscitation.

13. The method according to claim 12, further comprising:
terminating the fluid challenge in response to the fluid responsiveness probability value indicative of the associated patient being non-responsive to the fluid resuscitation.

14. The method according to claim 13, further comprising:
receiving baseline physiological signals from the plurality of physiological monitors of the associated patient prior to initiation of the fluid challenge; and
calculating at least one of a plurality of dynamic indices and/or features from the baseline physiological signal signals in accordance with the baseline dynamic indices and/or features and the fluid challenge dynamic indices and/or features.

15. The method according to claim 14, wherein calculating the fluid responsiveness probability value further comprises:
applying the one or more dynamic indices and/or features from the synchronized plurality of physiological signals and the one or more dynamic indices and/or features from the baseline physiological signals into a classification algorithm.

16. The method according to claim 12, further comprising:
generating an alarm responsive to the fluid responsiveness probability value indicative of the associated patient being non-responsive to the fluid resuscitation.

17. The method according to claim 12, further comprising:
generating a display of a likelihood of responding to the fluid resuscitation of the associated patient responsive to the calculated fluid responsiveness probability value.

18. The method according to claim 12, wherein the dynamic indices and/or features comprise at least one of a pulse pressure variability (PPV), a stroke volume variability (SVV), a systolic pressure variability (SPV), a RR variability (RRV), and a pleth variability index (PVI).

19. A computer medium storing instructions executable to control a computer and a display to perform the method of claim 12.

20. A system configured to assess the fluid responsiveness of an associated patient to fluid resuscitation including a processor programmed to perform the method of claim 12.

* * * * *